United States Patent
Buch-Rasmussen et al.

(10) Patent No.: US 6,755,810 B1
(45) Date of Patent: Jun. 29, 2004

(54) MEDICAMENT TRANSFERRING DEVICE

(75) Inventors: Thomas Buch-Rasmussen, Gentofte (DK); Jens-Ulrik Poulsen, Virum (DK); Henrik Ljunggreen, Ballerup (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/856,258

(22) PCT Filed: Nov. 16, 1999

(86) PCT No.: PCT/DK99/00629

§ 371 (c)(1),
(2), (4) Date: Sep. 20, 2001

(87) PCT Pub. No.: WO00/28940

PCT Pub. Date: May 25, 2000

Related U.S. Application Data
(60) Provisional application No. 60/110,747, filed on Dec. 3, 1998.

(30) Foreign Application Priority Data

Nov. 17, 1998 (DK) ........................................ 1998-01502

(51) Int. Cl.[7] .................................................. A61M 5/32
(52) U.S. Cl. ....................................................... 604/415
(58) Field of Search ................................ 604/187, 186, 604/183, 181, 200–207, 210, 415

(56) References Cited

U.S. PATENT DOCUMENTS

| | | | |
|---|---|---|---|
| 4,936,833 A | * 6/1990 | Sams | 604/232 |
| 5,112,317 A | * 5/1992 | Michel | 604/208 |
| 5,220,948 A | 6/1993 | Haber et al. | 604/407 |
| 5,279,585 A | * 1/1994 | Balkwill | 604/207 |
| 5,292,318 A | 3/1994 | Haber et al. | 604/407 |
| 5,304,152 A | * 4/1994 | Sams | 604/207 |
| 5,545,144 A | 8/1996 | Fryklund et al. | |
| 5,688,251 A | * 11/1997 | Chanoch | 604/208 |
| 5,961,495 A | * 10/1999 | Walters et al. | 604/208 |

FOREIGN PATENT DOCUMENTS

| | | | |
|---|---|---|---|
| EP | 0/499 764 A1 | 8/1991 | A61J/1/20 |
| NO | 177037 | 3/1989 | A61J/1/20 |
| WO | WO 96/26702 | 2/1996 | A61J/1/20 |
| WO | WO 98/02129 | 6/1997 | A61J/1/20 |

* cited by examiner

*Primary Examiner*—Manuel Mendez
*Assistant Examiner*—Kevin C. Sirmons
(74) *Attorney, Agent, or Firm*—Reza Green, Esq.; Richard W. Bosk, Esq.; Marc A. Began, Esq.

(57) ABSTRACT

The present invention relates to a transfer device for transferring medicament from a medicament container to a syringe with a needle. The transfer device is arranged for transferring accurate dosages of insulin, growth hormone or other medicaments. The accuracy is ensured by the device comprising means for mounting a syringe to the device, the needle piercing a sealing of the device. Opposite the sealing a piston is arranged, said piston being non-releasable engaged with the piston driver during transfer of the medicament. Thereby the piston is not erroneously drawn from the piston driver, which would otherwise lead to incorrect dosing. Furthermore, the device comprises dosing means including the piston driver.

12 Claims, 4 Drawing Sheets

MEDICAMENT TRANSFERRING DEVICE

This application is a 371 of PCT 10K99/00629 field Nov. 16, 1999 which claims benefit of 60/110,747 filed Dec. 3, 1998.

The present invention relates to a transfer device for transferring medicaments to a syringe with needle as well as a method for filling syringes.

PRIOR ART

Some patients may parentally administer medicaments on a regular basis. Medicaments, such as insulin or growth hormone, are very important to dose accurately. Often the dose is aspirated from a vial to a calibrated syringe, and due to the potency of the medicament it is important that the amount of the medicament aspirated into the syringe for each dose is precise. The accuracy depends on a variety of factors, such as the calibration of the syringe, the patient's vision as well as general motoric abilities to precisely dose the medicament.

To encrease the accuracy several dosage measuring devices have been presented wherein the calibration is carried out by an apparatus whereby the medicament is expelled into the syringe from a vial. In some systems a syringe is coupled to a vial or container and the needle cannula on the syringe is piercing a piston of the vial or container, whereby a force driving the syringe into the container presses the medicament in the container into the syringe via the needle.

For example, WO 93/02723 discloses a syringe-filling mechanism wherein a syringe held within a syringe holder is filled from a container including a piston mounted within a container. The syringe holder is threadably mounted to the vial with the needle cannula piercing the piston to permit the syringe holder to be driven against the piston in a controllable way to meter the pharmaceutical introduced into the syringe. By this mechanism the piston must allow several piercings without leakage. In practice it has proved a problem to design a material for a piston which is of sufficient strength to act as the piston while also being enough flexible to be pierced several times without leaking.

Other systems comprise a container comprising a piston and opposite the piston a sealing. The needle cannula then pierces the sealing and the medicament is forced into the syringe via the needle by driving the piston towards the sealing.

An example hereof is the system of WO 93/02921 disclosing a device wherein the piston is provided at the end of the container opposite the syringe holder. Thereby the piston material may not necessarily be pierceable. However, this kind of system exhibits another problem, namely that the piston may be drawn from the piston driver, if the person using the system, draw the syringe plunger rod before releasing the syringe from the syringe holder. This will lead to an uncorrect larger dosage in the syringe. Next time the person is dosing a smaller dosage is metered because the first part of the dosing movement will lead the container piston rod to abut the piston again and only thereafter the dosing movement will move the piston to fill the syringe.

SUMMARY OF THE INVENTION

The present invention is related to a device, wherein the above problems have been solved and which permits even an untrained person to easily and accurately fill a syringe with the correct dose of a liquid medicament.

Accordingly in one aspect, the present invention relates to a transfer device for transferring medicament from a medicament container to a syringe with a needle, comprising a medicament container having one end sealed with a pierceable sealing, and a piston slidably arranged within the container, means for mounting the syringe to the device with the needle piercing the sealing, the device further comprising dosing means including a piston driver, said dosing means being adapted for forwards calibrated movement for transferring medicament from the container to the syringe via the needle, and wherein the piston driver is adapted to be non-releasably engaged with the piston during transfer of the medicament.

The container forms an enclosed chamber filled with the medicament liquid and has the open end closed by a piston. The piston is slidable longitudinally relative to the container, and the piston is in fluid-tight connection with the container wall in any position of the piston sliding movement.

The device according to the invention is thus constructed to secure that the piston will not move forwards if the patient by mistake draws the syringe plunger rod before the needle is removed from the sealing. Accordingly, the piston can only move forwards when driven by the piston driver during activation of the dosing means. The term "during transfer" refer to the situation where the syringe is coupled to the device with the needle piercing the sealing, i.e. the situation wherein the route for transferring medicament to the syringe is intact. Thereby, a very safe, reliable and precise transfer device is provided.

The piston is driven forwards by a piston driver into the container by a movement corresponding to the dose to be transferred into the syringe.

In one embodiment the piston may be coupled to the piston driver by engagement means. The engagement means may be any suitable means, such as a snap lock, a threaded coupling, a bajonet lock, a luer lock or a suitable combination thereof or any other coupling that secure that the piston is engaged to the piston driver during transfer.

The snap lock may be a rotatable snap lock, whereby rotation of the piston driver is not transmitted as rotation of the piston during dosing. In another embodiment the snap lock may be a unidirectional, rotatable snap lock.

In a further embodiment the piston is integrated with the piston driver. The integration process may be carried out by any suitable process known to the skilled person. The piston may be moulded onto the piston driver by a two-component moulding process, or the piston may be moulded of the same material as the piston driver in one process. In the latter case, the fluid-tight engagement of the piston to the container wall may be secured by an O-ring on the piston.

Integration can also be carried out be applying glue or adhesive on the part of the piston driver abutting the piston, whereby when inserting the piston driver into the container, the piston and the piston driver are connected and remain so for the lifetime of the container.

Furthermore, the piston and the piston driver may be welded together for permanent engagement.

The piston is moved or forced forwards by the piston driver, which is acitiviated by the dosing means. The dosing means may be connected to the piston driver by means of a welding process, a gluing process, or a moulding process. In a preferred embodiment the dosing means is moulded unitarily with the piston driver. This reduces the amounts of parts to be produced for the device, and furthermore, the transmission chain from the dosing means to the piston is shortened which diminishes the variations in the dosing quantities.

The dosing means is coupled to the container in any suitable manner allowing the dosing means to activate the piston driver moving the piston forwards. Preferably, the dosing means is coupled through a threaded coupling to the container so that rotating the dosing means in a rotary direction relative to the container drives the piston in the container towards the sealing end of the container.

In the present context, the movement towards the sealing is denoted forwards movement. The movement is calibrated, which in a preferred embodiment is made by providing the device with means for precisely indicating the volume of medicament which has been transferred from the vial to the syringe. The amount of medicament delivered into the syringe may be indicated in several ways. The amount can be easily and precisely controlled by controlling the number of full and partial revolutions of the dosing means relative to the vial. The control is eased by providing an audible sound for each partial revolution, e.g. a click per unit of medicament.

The indication may be carried out in any suitable way as is apparent to the skilled person. In a preferred embodiment the indication is provided by including at least one detent lock protruding from the container and at least one ridge axially extending along the outer surface of the piston driver. The detent ridge sized and positioned to engage the detent lock each time the dosing means is rotated a set distance. In a further preferred embodiment at least two detent locks are provided opposite each other whereby a rotation half-way the circumference of the container is indicated by a click sound, for example. However, the detent lock also may be positioned on the piston or the piston driver, or even elsewhere on the dosing means, the requirement only being that the ridge is positioned correspondingly on a part of the device passing the detent lock on activating the dosing means.

The number of detent locks and/or ridges may be adjusted to the purpose of the container, i.e. the medicament to be transferred. In a most preferred embodiment at least ten units of medicaments are indicated during a full rotation of the dosing means, even more preferred twenty doses. This may be carried out by arranging 10 (20) ridges on the piston driver combined with one or two (even three) detent locks. Another example would be 10 to 20 detent locks and 1–3 ridges.

The container may be arranged in a housing, whereby the dosing means may be coupled to the housing instead of the container itself. However, in a preferred embodiment, in order to reduce the amount of parts to be assembled for the device, the container is produced, preferably moulded, in a manner providing the container with coupling means for coupling the dosing means directly to the container.

In order to further secure an accurate dosing mechanism for each dose transferred from the container, it is of importance to prevent backward movement of the piston driver. Accordingly, the dosing means may be provided with locking means.

The locking means may be any means preventing the backward movement of the piston driver. In a preferred embodiment the locking means are included in the detent lock described above. Using the detent lock for locking means as well, it is preferred to arrange at least two detents on the container to give a more secure engagement of the dosing means in relation to the piston while the device is not in use.

In another preferred embodiment the locking means are provided by arranging detent locks on the inner face of the dosing means corresponding to the threaded coupling on the container. Thereby, the coupling is functionally a unidirectionaly threaded coupling. In yet another embodiment the locking means are provided in the piston, such as metallic spring(s) inhibiting backward movement of the piston and thereby the piston driver.

Alternatively, the detent locks may be provided as locking means only, whereby the indication means may be a scale on the outside of the container and/or dosing means with an indication for each unit of medicament. A combination of a scale and audible indication means are also envisaged by the present invention.

The syringe may be any syringe, such as a hypodermic syringe. The syringe may be non-calibrated in that the calibration and the dosing is conducted by the transfer device. Thereby, the device provides a very economic system because non-calibrated syringes are sold at much lower prices than calibrated syringes.

The needle on the syringe may be fixedly attached to the syringe or may be releasable. Any needle suitable for injections may be used. Preferably the same needle is used for transferring the medicament and for injecting the medicament to the patient. Accordingly, any needle normally used for injections may be applied to the syringe.

In a preferred embodiment the needle is integrated in the syringe. Thereby the excess space in the needle and coupling between the needle and the syringe is diminished. This will lead to a more precise dosing in that only a small amount of air inherently present in the syringe/needle will interfere with dosage during injection.

The syringe may be mounted to the device by means of a syringe holder, such as a housing having a central bore, wherein the syringe is mounted pointing the needle towards the sealing of the container. The syringe holder may be coupled to the container via any suitable coupling means, such as a snap lock, a threaded coupling, a bajonet lock, a luer lock or a suitable combination thereof. The syringe holder may be releasably coupled to the container, whereby the syringe holder can be reused after emptying the container. In another embodiment, the syringe holder may be unitarily moulded with the container to reduce the amount of parts to be assembled after the moulding process.

However, in a further embodiment the syringe is coupled directly to the container by means of a releasable coupling, such as a releaseable snap lock, a threaded coupling, a bajonet lock, a luer lock or a suitable combination thereof. In this case means for directing the needle towards the sealing of the container is preferably provided.

The normal dosage for a patient in need of insulin is from 1 to 70 units, which for most insulin formulations correspond to about 0,01 to 0,7 ml per dosage, with an average of about 10 units. The multi-dose container preferably contains a volume of medicament suitable for dosages for several days, such as from 1 to 10 ml, preferably from 3 to 10 ml. Accordingly, the container comprises at least two dosages of medicament. Therefore, the sealing of the container must be adapted to being repeatedly pierced by a needle without leaking any medicament in between the transfer of medicaments.

Another object of the present invention is a method for filling a syringe having a needle with medicament from a container, using a device as defined above, comprising coupling a syringe-to the device with the needle piercing the sealing of the container, activating the dosing means to drive the piston towards the sealing, transferring medicament from the container to the syringe via the needle, and removing the syringe containing medicament from the device after the transfer has been finalised. The syringe then contains the correct amount of medicament corresponding to the amount metered by the dosing means, and the syringe is ready for injecting the medicament to the patient in need thereof.

When the container is empty it may be replaced with a container filled with medicament, reusing the dosing means and the syringe holder, which may be mounted on the filled container. In another embodiment the container is discarded together with the dosing means and/or the syringe holder.

DRAWINGS

DESCRIPTION OF THE INVENTION

In the following the invention is described in greater detail referring to the figures.

Figure 1:
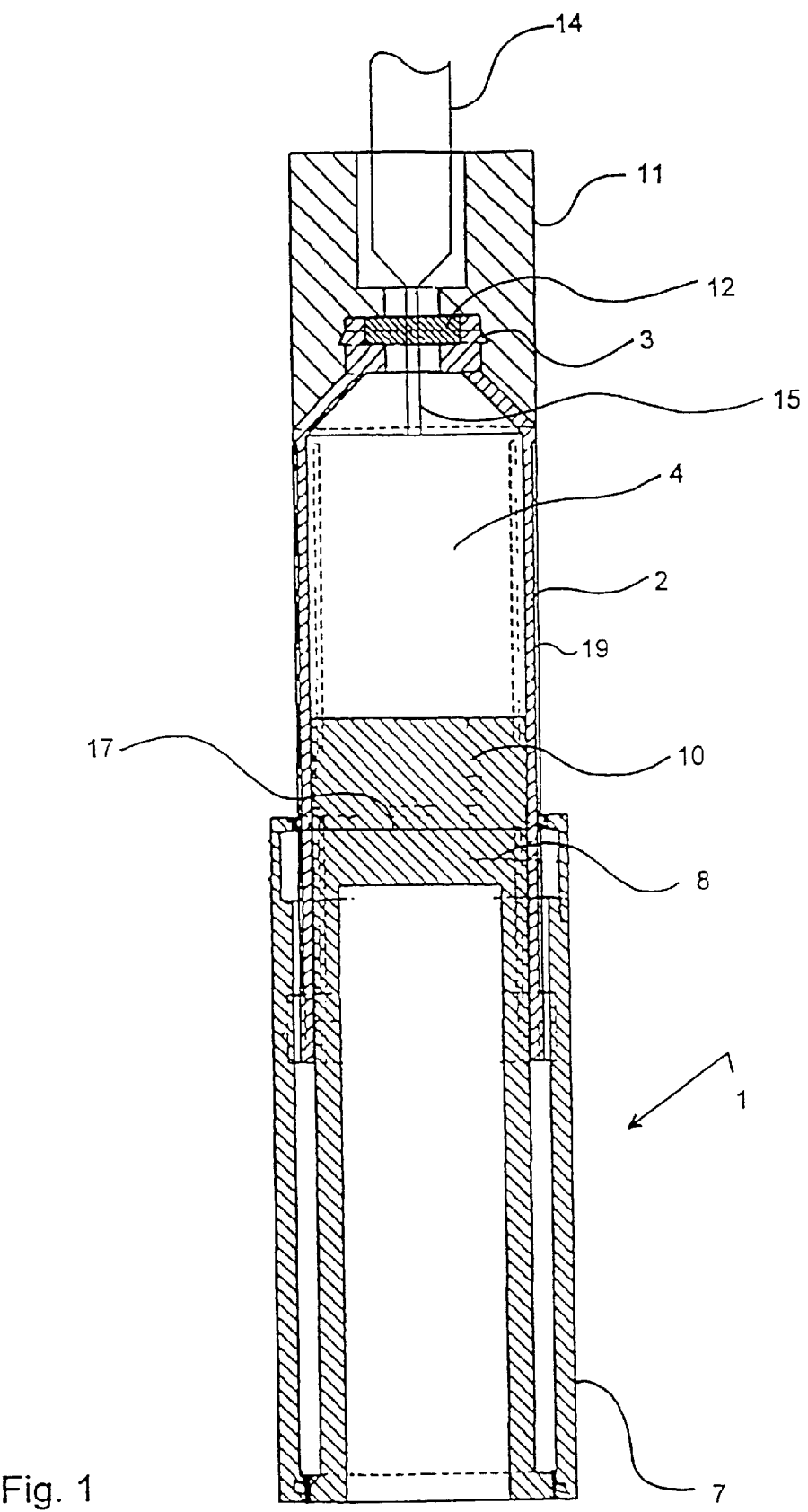
FIG. 1 is a schematic view of the device according to the invention in a transfer situation comprising a syringe with a needle piercing the sealing.

FIG. 1 shows the device 1 with the container 2 comprising one end with coupling means 3 for the syringe holder 11, said end being sealed with a sealing 12. The interior lumen 4 of the container is containing the medicament. FIG. 1 further shows the dosing means 7 mounted to the container 2 via a threaded coupling. Furthermore, container 2 comprises piston 10 moulded to by two-component process to the piston driver 8, the coupling between the piston and the piston driver is denoted 17. The piston is in slidable fluid-tight engagement with the container wall 19. The piston may be produced from any suitable material, such a rubber or a flexible plastic material.

In the syringe holder 1 the syringe 14 is mounted with the needle 15 piercing the sealing 12. In this position the device 1 is ready for dosing the correct amount of medicament from the container 2 to the syringe 14, by rotating the dosing means 7 with respect to the container.

Figure 2:
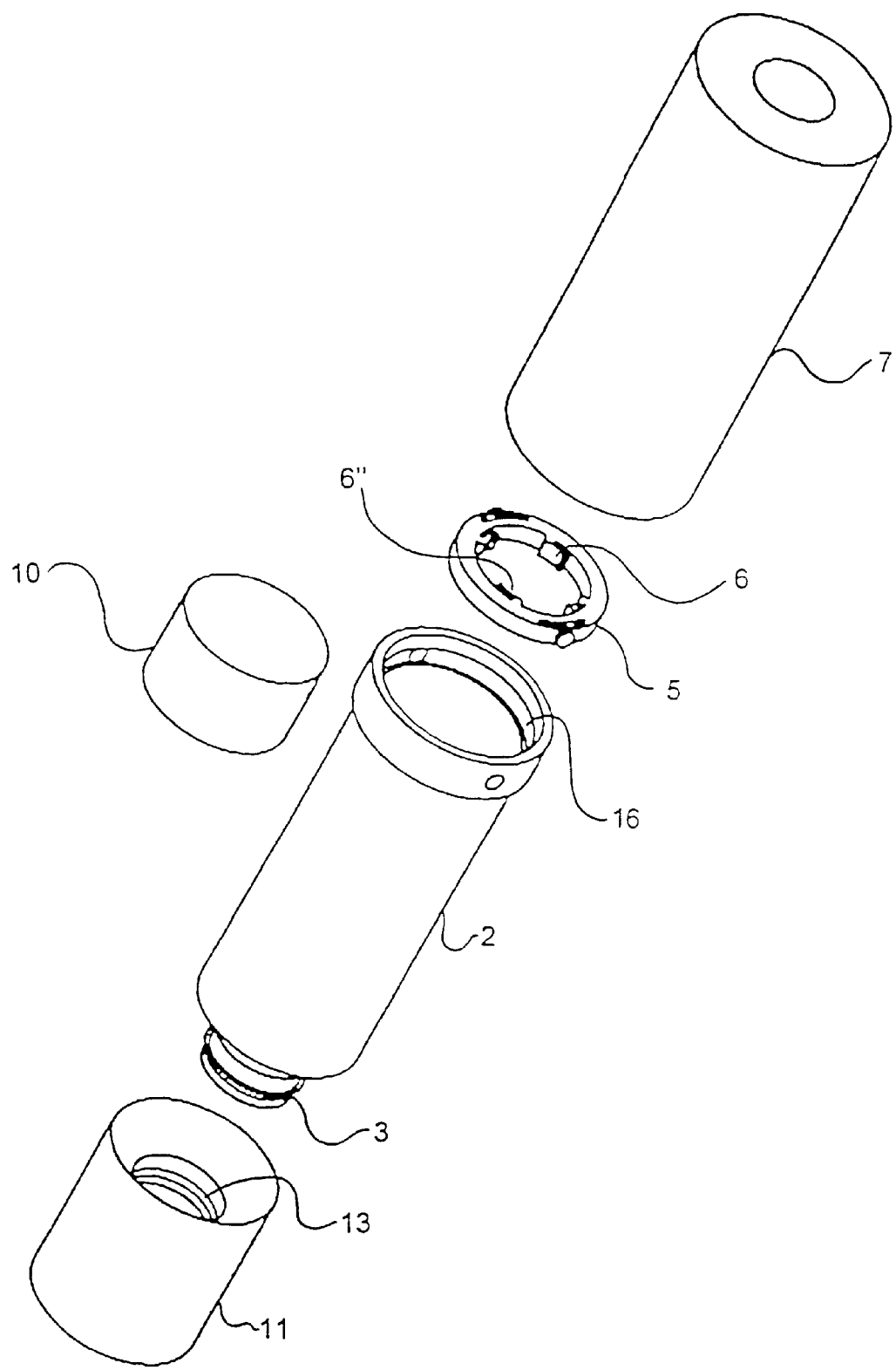
FIG. 2 is showing the device of FIG. 1 in greater detail.

FIG. 2 shows the various parts of the device 1 in greater detail. A ring 5 having two detent locks 6' and 6" is adapted to be mounted to the container 2 to provide the container with locking means. The ring 5 is located in a recess 16 moulded in the end of the container opposite the sealing. The piston 10 is inserted into the end of the container 2 opposite the sealing to close the container 2 after filling the medicament into the container 2.

After insertion of the piston 10 the dosing means 7 may be coupled to the container 2, and the device 1 is ready for use.

The syringe holder 11 comprises threads 13 for engagement with the coupling means 3.

Figure 3:
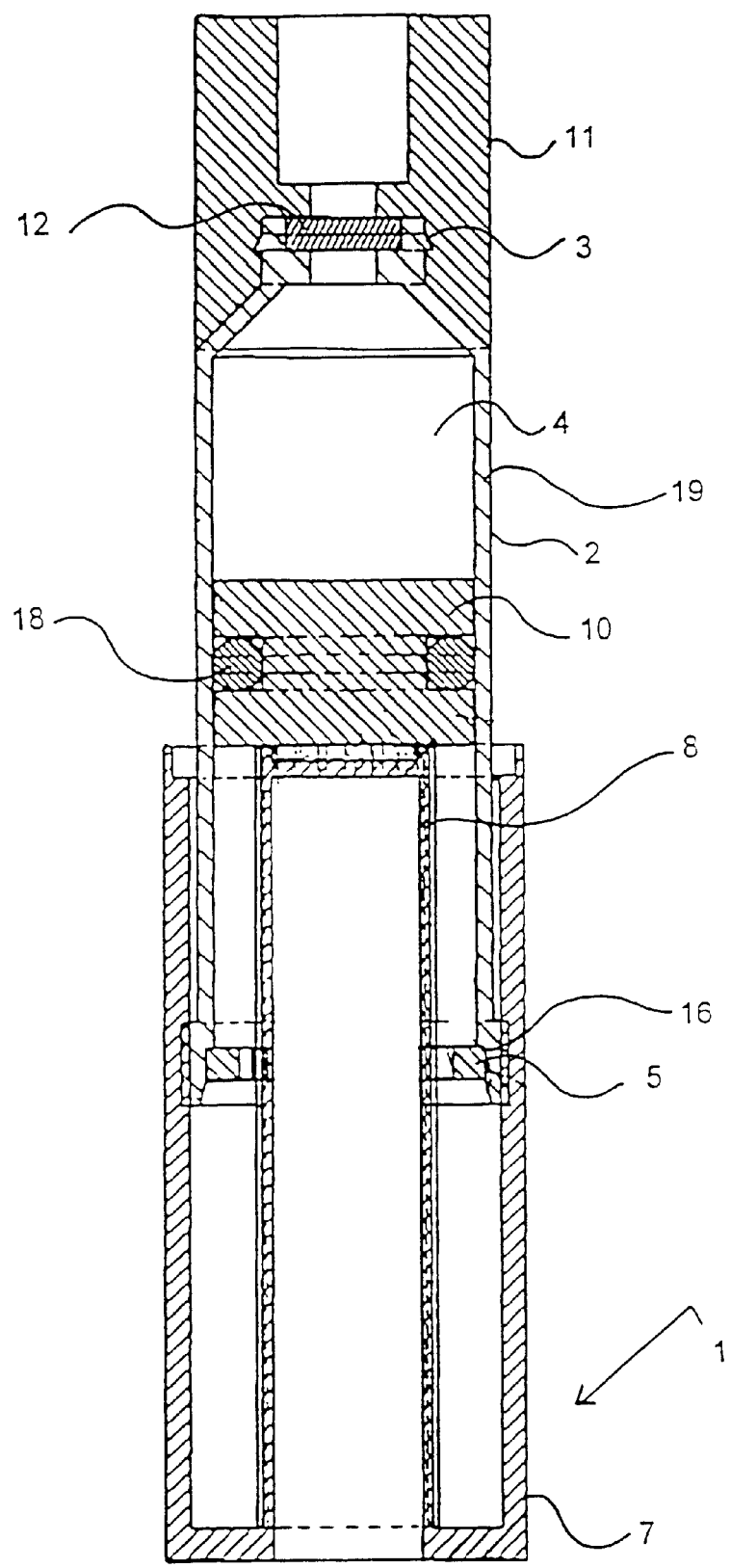
FIG. 3 shows another embodiment of the device.

FIG. 3 shows a device 1 as in FIG. 1, however in FIG. 3 the piston driver 8 is unitarily moulded with the dosing means 7. Furthermore, the piston driver 8 is snapped on the piston 10. The fluid-tight engagement is secured by the O-ring 18 surrounding the piston 10. The O-ring may be made of any flexible material, such as rubber or plastic. By the use of an O-ring the requirements to the piston material is reduced, the piston 10 may be produced of any suitable material, even a non-flexible material, such as the plastic material used for the piston driver 8.

Figure 4:
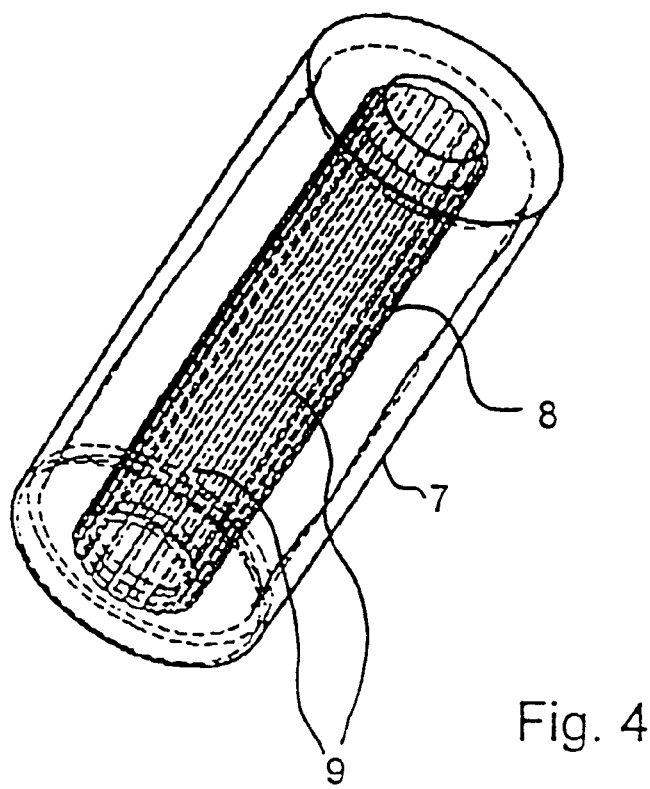
FIG. 4 shows the details of the dosing means of the device according to FIG. 3.

FIG. 4 shows interior details of a dosing means 7 for the device 1 of FIG. 3 comprising the piston driver 8. The piston driver 8 is provided with 20 ridges 9 to engage the detent lock 6', 6" on the container 2, whereby an audible click is made for each unit transferred corresponding to each partly rotation.

Figure 5:
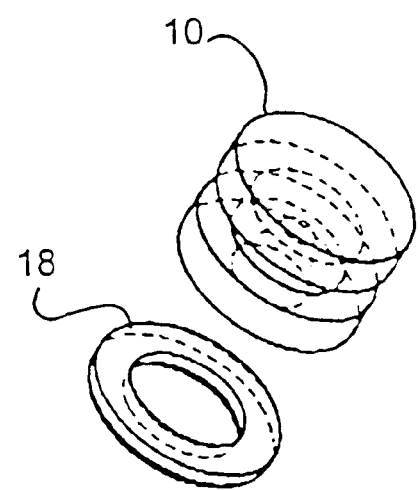
FIG. 5 shows the piston with O-ring.

FIG. 5 shows a piston 10 with a recess for receiving the O-ring 18.

What is claimed is:

1. A transfer device for transferring medicament from a medicament vial to a syringe with a needle, comprising a medicament vial having one end sealed with a pierceable sealing, and a piston slidably arranged within the vial, means for mounting the syringe to the device with the needle piercing the sealing, the device further comprising a dosing means including a piston driver, said dosing means being adapted for forwards calibrated movement for transferring medicament from the vial to the syringe via the needle, characterised in that the piston driver is adapted to be non-releasably engaged with the piston during transfer of the medicament, wherein the piston driver is coupled to the piston by engagement means.

2. The device according to claim 1, wherein the engagement means is a snap lock.

3. The device according to claim 2, wherein the snap lock is a rotatable snap lock.

4. A transfer device for transferring medicament from a medicament vial to a syringe with a needle, comprising a medicament vial having one end sealed with a pierceable sealing, and a piston slidably arranged within the vial, means for mounting the syringe to the device with the needle piercing the sealing, the device further comprising a dosing means including a piston driver, said dosing means being adapted for forwards calibrated movement for transferring medicament from the vial to the syringe via the needle, characterised in that the piston driver is adapted to be non-releasably engaged with the piston during transfer of the medicament wherein the piston is moulded with the piston driver.

5. The device according to claim 1, wherein the dosing means is coupled through a threaded coupling to the vial so that rotating the dosing means in a rotary direction relative to the vial drives the piston in the vial towards the sealing end of the vial.

6. The device according to claim 1, wherein the piston driver is unitarily moulded with the dosing means.

7. The device according to claim 1, wherein the vial is arranged in a housing.

8. The device according to claim 7, wherein the dosing means is coupled to the housing.

9. The device according to claim 1, wherein the dosing means is provided with locking means for preventing backward movement of the piston driver.

10. The device according to claim 9, wherein the locking means is included in the detent lock indicating the medicament transferred.

11. The device according to claim 1, wherein the piston comprises an O-ring.

12. A transfer device for transferring medicament from a medicament vial to a syringe with a needle, comprising a medicament vial having one end sealed with a pierceable sealing, and a piston slidably arranged within the vial, means for mounting the syringe to the device with the needle piercing the sealing, the device further comprising a dosing means including a piston driver, said dosing means being adapted for forwards calibrated movement for transferring medicament from the vial to the syringe via the needle, characterised in that the piston driver is adapted to be non-releasably engaged with the piston during transfer of the medicament wherein the device comprises means for precisely indicating the volume of medicament which as been transferred from the vial to the syringe, and wherein the indicating means includes at least one detent lock at the vial and at least one ridge on the piston driver.

* * * * *